(12) United States Patent
Fisher

(10) Patent No.: US 12,358,816 B2
(45) Date of Patent: Jul. 15, 2025

(54) WATER TREATMENT DEVICE

(71) Applicant: Timothy John Fisher, Cranbourne (AU)

(72) Inventor: Timothy John Fisher, Cranbourne (AU)

( * ) Notice: Subject to any disclaimer, the term of this patent is extended or adjusted under 35 U.S.C. 154(b) by 326 days.

(21) Appl. No.: 17/441,412

(22) PCT Filed: Apr. 14, 2020

(86) PCT No.: PCT/AU2020/000032
§ 371 (c)(1),
(2) Date: Sep. 21, 2021

(87) PCT Pub. No.: WO2020/206490
PCT Pub. Date: Oct. 15, 2020

(65) Prior Publication Data
US 2022/0177330 A1    Jun. 9, 2022

(30) Foreign Application Priority Data

Apr. 11, 2019  (AU) ................... 2019901257

(51) Int. Cl.
*C02F 1/32* (2023.01)
*G01N 21/59* (2006.01)

(52) U.S. Cl.
CPC ............. *C02F 1/325* (2013.01); *G01N 21/59* (2013.01); *C02F 2201/3226* (2013.01); *C02F 2201/324* (2013.01)

(58) Field of Classification Search
None
See application file for complete search history.

(56) References Cited

U.S. PATENT DOCUMENTS

| | | |
|---|---|---|
| 5,120,450 A | 6/1992 | Stanley, Jr. |
| 5,900,211 A | 5/1999 | Dunn et al. |
| 8,907,302 B2 * | 12/2014 | Anton .................. B01J 19/123 250/435 |
| 9,056,147 B2 | 6/2015 | Ma |
| 2002/0079271 A1 | 6/2002 | Baca |

(Continued)

FOREIGN PATENT DOCUMENTS

| | | | |
|---|---|---|---|
| CN | 101790764 B * | 1/2013 | ............ B82Y 10/00 |
| CN | 105672491 B * | 1/2018 | |

(Continued)

*Primary Examiner* — Andrew Smyth
(74) *Attorney, Agent, or Firm* — Millen, White, Zelano & Branigan; Christopher W. Brody

(57) ABSTRACT

A disinfection device including a pipe with a taper, inlet, and outlet; an ultraviolet laser; a beam steering device and a transparent layer. The laser, located at a smaller diameter end of the pipe, projects a laser beam towards a larger diameter end of the pipe. The laser beam projects through and/or off the beam steering device and through the transparent layer at a plurality of angles in a cycle. The beam steering device reflects, refracts and/or deflects the laser beam at angles such that a laser beam profile projects through part or all of an inner profile of any point along the taper in the cycle. The pipe receives a fluid that passes through the pipe. One of the inlet or the outlet is located at the smaller diameter pipe end and the other of the inlet or the outlet is located at the larger diameter pipe end.

23 Claims, 11 Drawing Sheets

(56)  References Cited

U.S. PATENT DOCUMENTS

| | | | |
|---|---|---|---|
| 2003/0217978 A1 | 11/2003 | Safta | |
| 2006/0165563 A1* | 7/2006 | Berry | A61L 2/08 |
| | | | 422/121 |
| 2012/0168641 A1 | 7/2012 | Lizotte | |
| 2012/0196011 A1* | 8/2012 | Felix | A23B 2/53 |
| | | | 426/243 |
| 2015/0048260 A1 | 2/2015 | Chui et al. | |
| 2017/0217792 A1* | 8/2017 | Dajnowski | C02F 1/325 |
| 2019/0142987 A1* | 5/2019 | Zhang | A61L 2/26 |
| | | | 250/435 |

FOREIGN PATENT DOCUMENTS

| | | | | |
|---|---|---|---|---|
| CN | 207726769 U | * | 8/2018 | |
| DE | 19908583 C2 | * | 10/2002 | G01N 21/33 |
| EP | 0019211 | | 11/1980 | |
| GB | 2316528 | | 2/1998 | |
| JP | 2007-217096 | | 8/2007 | |
| KR | 20170039929 A | * | 4/2017 | |
| WO | 2010/093698 | | 8/2010 | |
| WO | WO-2010093698 A1 | * | 8/2010 | C02F 1/325 |

\* cited by examiner

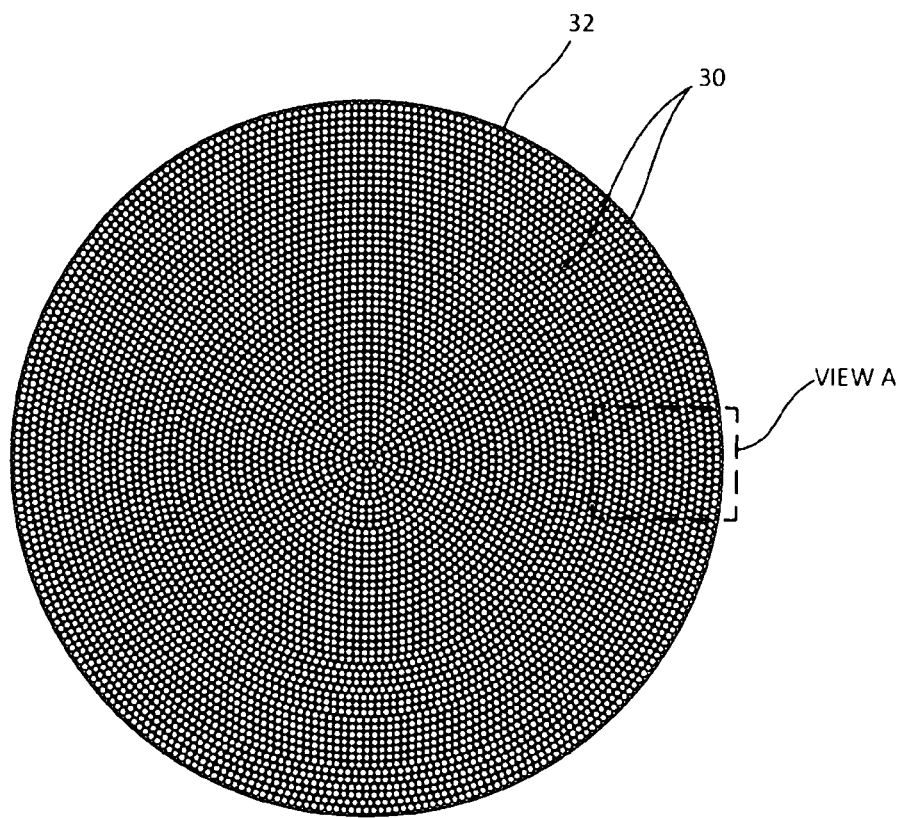
Fig. 9
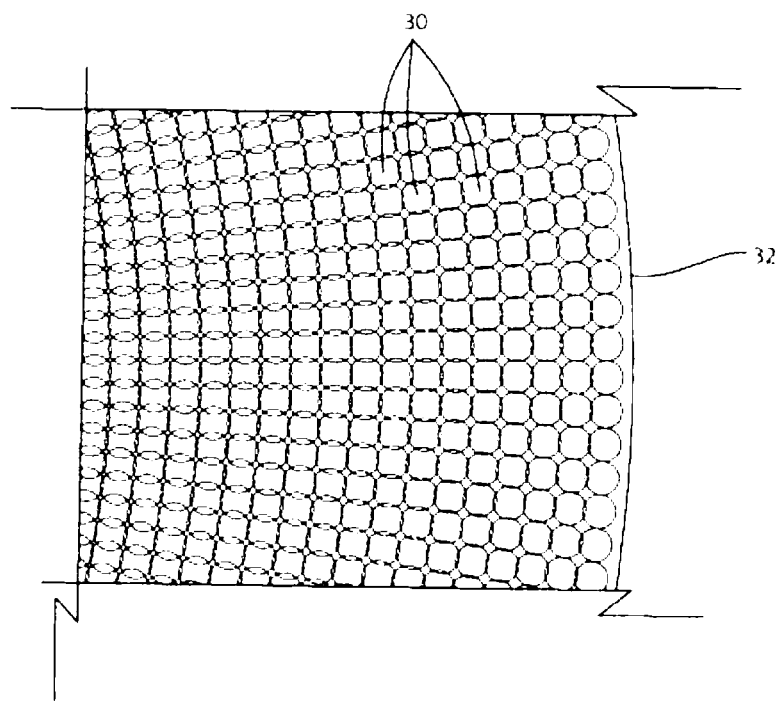
Fig. 10 (View A)

WATER TREATMENT DEVICE

FIELD OF INVENTION

This invention relates to a disinfection device for water treatment. More particularly, this invention relates to a steered ultraviolet laser disinfection device.

BACKGROUND ART

The following references to and descriptions of prior proposals or products are not intended to be, and are not to be construed as, statements or admissions of common general knowledge in the art. In particular, the following prior art discussion should not be assumed to relate to what is commonly or well known by the person skilled in the art, but to assist in the inventive process undertaken by the inventor(s) and in the understanding of the invention.

Disinfection devices for water treatment have been described using incandescent or led ultraviolet (UV) lamps. These lamps are mounted within a pressure vessel, the untreated fluid passes through the pressure vessel and is exposed to UV light emitted by the lamps. The lamps (or transparent lamp cover) need to be cleaned intermittently to ensure significant UV radiation is passing through the water within the vessel.

An object of the present invention is to ameliorate one or more of the aforementioned disadvantages of the prior art or to at least provide a useful alternative thereto.

STATEMENT OF INVENTION

The invention according to one or more aspects may be as defined in the independent claims. Some optional and/or preferred features of the invention are defined in the dependent claims.

Accordingly, in one aspect of the invention there is provided:

A disinfection device including a pipe, an ultraviolet (UV) laser, a beam steering device and a transparent layer, the pipe including a tapered section, an inlet and an outlet, wherein:
- the UV laser is located at a smaller diameter end of the pipe and is adapted to project a laser beam towards a larger diameter end of the pipe;
- the laser beam is adapted to project through and/or off the beam steering device and through the transparent layer at a plurality of angles in a cycle;
- the beam steering device is adapted to reflect, refract and/or deflect the laser beam at the angles such that the laser beam projects through part or all of an inner profile of a point along the tapered section in the cycle;
- the pipe is adapted to receive a fluid that enters the inlet, passes through the pipe and exits through the outlet; and
- one of the inlet or outlet is located at the smaller end of the pipe and the other of the inlet or the outlet is located at the larger end of the pipe.

Disinfection Device

Multiple disinfection devices may be installed in series or in parallel. Preferably, the disinfection device forms part of a larger pipe network.

Pipe

The pipe may be nominated a main pipe. The pipe may be plastic, metal or a composite. Preferably, the pipe is metal. Most preferably, the pipe is stainless steel. The pipe defines one or more internal walls. The internal walls of the pipe may be reflective.

The pipe may be made of a single piece. The pipe may be made of multiple pieces (or sections). Preferably, the pipe is made of multiple pieces. The multiple pieces may be joined together with bolts, screws, nuts and/or other attachment means. Preferably, the multiple pieces are joined together with bolts. Preferably, the pipe has flanges on each of the multiple pieces which abut against each other and include holes to receive bolts to join the multiple pieces.

The pipe may include fins or channels to keep the flow through the pipe laminar. Preferably, the pipe includes channels. Preferably, the channels are made of concentric truncated cones held concentrically with radial panels. The channels may be made of square channels. The fins may protrude from inner surfaces of the pipe. The channels may extend the length of the tapered section or the length of the pipe. Preferably, the channels extend part of the length of the tapered section.

There may be multiple tapered sections in the pipe. For example, there may be two tapered sections with a beam deflector between them to redirect the laser beam to follow the profile of the second tapered section.

The length of the pipe may be any one of a variety of lengths, at least to some extent, depending on the application. The length of the pipe may be between 200 mm and 10 m. Preferably, the length of the pipe is between 300 mm and 2400 mm. Most preferably, the length of the pipe is 1500-2000 mm, and may typically be about or precisely 1800 mm. Preferably, the length of the pipe may be at least 500 mm. The diameter of the smaller end of the pipe is at least smaller than that of the larger end.

Ultraviolet Laser

The wavelength of the light from the UV laser may be between 10 nm and 400 nm. Preferably, the wavelength of light which projects from the ultraviolet laser is between 100 nm and 300 nm. The input power of the ultraviolet laser may be any power. Preferably, the input power of the ultraviolet laser is between 200 mW and 2 W.

Preferably, the size of the profile of the laser beam is at least 1 mm. The laser beam preferably round in profile, the size of the beam profile will be measured in terms of its diameter. Preferably, the larger the diameter of the pipe, the larger the size of the laser beam profile.

The disinfection device may include a mirror at the larger diameter end of the pipe to reflect the laser beams back down the length of the pipe. The mirror may be flat, convex, concave, conical or other shapes. Preferably, the mirror is a concave mirror. The concave mirror may have a concave mirror cleaner. The concave mirror cleaner may use a mechanical device such as a wiper to clean the concave mirror. The concave mirror cleaner may use compressed fluid (such as a fast stream of fluid directed at a concave mirror surface) to clean the concave mirror. Preferably, the concave mirror is made of materials including aluminium or aluminium alloy.

Preferably, the disinfection device includes a UV sensor at the larger diameter end of the pipe. Preferably, the UV sensor is positioned in line with a longitudinal axis of the tapered section. The UV sensor may assist in calibrating the beam steering device. The UV sensor may assist in measuring the build up of material on the transparent layer. Preferably, the UV sensor can detect when the UV laser is off or ineffective (for example due to a malfunction). Preferably, the UV sensor can detect the brightness, intensity, or otherwise the efficacy, of the laser beam.

The disinfection device may include a second laser which is adapted to burn and therefore clean debris off the transparent layer and/or mirror. The second laser may not include a UV laser. The second laser may require more input power or be a more powerful laser than the UV laser. Alternatively, the UV laser may be adapted to switch to a higher output power or higher output intensity to burn debris off the transparent layer and/or mirror.

Beam Steering Device

The beam steering device may include at least one mirror. The beam steering device may include multiple mirrors or other directional devices capable of steering or redirecting the laser beam with little or no loss of intensity at the zone of re-direction or reflection. The beam steering device may include a Risley prism system. Preferably, the beam steering device includes 2 mirrors to reflect the laser beam at a required angle. The beam steering device may include the transparent layer. The beam steering device may include other transparent layers, such as glass layers before and after the mirrors of the beam steering device. Preferably, the glass layers are quartzite.

Preferably, the beam steering device includes electric motors. Preferably, the electric motors move the mirrors to reflect the laser beam at the required angle. The beam steering device may be controlled with a computer or other electric circuit. The beam steering device may include a computer. The beam steering device may be controlled through an external computer, for example the computer may be located at an operator's control panel.

Preferably, the computer controls and takes measurements from the UV sensor. Preferably, the computer uses the information from the UV sensor to calibrate the beam steering device.

The beam steering device may deflect and/or reflect the laser beam. Preferably, the beam steering device reflects the laser beam. The angles the beam steering device reflects the laser beam at may be parallel to the longitudinal axis of the tapered section. The angles may be any radial angle (extending radially outwards from the longitudinal axis of the tapered section) up to the angle of the truncated cone walls of the tapered section and any rotational angle (rotating about the longitudinal axis of the tapered section). The angles may be any angle such that the laser beam shines through any point over the area of the inner profile of the tapered section. The angles may be a discrete set of angles. The angles may be a continuous range of angles. Preferably, the angles are a continuous range of angles.

Preferably, the inner profile of the tapered section is a 2-dimensional profile taken through a cross-section of the pipe. The inner profile may be defined by the internal surface of the tapered section. The internal surface may be or adapted to be in contact with the fluid. Preferably, the inner profile is normal (or perpendicular) to the longitudinal axis of the tapered section. Preferably, the point along the tapered section is a distance along the longitudinal axis of the tapered section. The laser beam may project through part or all of an inner profile of a point along the tapered section in a cycle. The laser beam may project through at least 90% of an inner profile of a point along the tapered section in the cycle. Preferably, the laser beam projects through at least 99% of an inner profile of a point along the tapered section in the cycle. Most preferably, the laser beam projects through 100% of an inner profile of a point along the tapered section in the cycle.

The time it takes to complete the cycle may vary depending on the application.

Preferably, the rate at which the laser beam is deflected between the angles is dependant on the size of the unit, the flow rate and diameter of the profile of the laser beam.

Transparent Layer

The transparent layer may include multiple layers. Preferably, the transparent layer includes one layer. The transparent layer may be made of materials including glass, plastic, quartz and quartzite.

Preferably, the transparent layer is made of quartzite. The transparent layer may include seals to seal the air in the beam steering device and around the UV laser from the fluid in the pipe. The seals may be made of materials including silicone seals, curable silicone adhesive, rubber, plastic, malleable metals or a similar material. The transparent layer may be held in place using a clamp mechanism, glue, screws, bolts or similar attachments.

Transparent Layer Cleaner

The disinfection device may also include a transparent layer cleaner. The transparent layer cleaner may include devices which project high pressure fluid at the transparent layer. The transparent layer cleaner may include mechanical wipers which contact the surface of the transparent layer in contact with the fluid. Preferably, the transparent layer cleaner includes mechanical wipers which contact the surface of the transparent layer in contact with the fluid. Preferably, the transparent layer cleaner includes electric motors. The transparent layer cleaner may be controlled with the same computer which controls the beam steering device or another computer (or electric circuit). Preferably, the transparent layer cleaner is controlled with the same computer which controls the beam steering device.

The transparent layer cleaner may include a sensor which detects when the transparent layer needs cleaning. The sensor may be the UV sensor. The transparent layer cleaner may be controlled with a tinier which activates the cleaning of the transparent layer after a time period. The computer may limit the sensor to be activated after a certain amount of time of use of the disinfection device, for example when the fluid is flowing through the pipe. Preferably, the cleaner time period is dependent on factors such as the type of fluid.

Tapered Section

The tapered section may have walls with an angle of above 0 and below 90 degrees from a longitudinal axis of the tapered section. The walls may be at angles of between 1 degree and 15 degrees. Preferably, the walls are at angles of between 3 and 5 degrees from the longitudinal axis of the tapered section. Preferably, the walls are truncated cone walls. Preferably, the walls are linear or straight in the direction of the longitudinal axis of the tapered section.

Preferably, a diameter of the walls at the smaller end is above 5 mm.

The tapered section may include any shaped 2-dimensional profile (inner profile) of a point along the cone shaped section. The inner profile may be circular, triangular, square, rectangular or any other shape. Preferably, the inner profile is circular. Preferably, the tapered section is a cone shaped section. The tapered section may be cone shaped on the inner surface of the tapered section and have other contours on the outer surface of the tapered section. The inner surface may include recesses of joins or longitudinal slots. The inner surface may include fins or holes. Preferably, the tapered section is cone shaped on the inner surface and cone shaped on the outer surface. The tapered section may be made of multiple parts joined together. The outer surface may include flanges to connect multiple parts of the tapered section. The tapered section may include bolts, screws or other fastening devices to join multiple parts of the tapered section together. The tapered section may include seals to seal the multiple parts of the tapered section together.

Preferably, the inner profile of the tapered section is the 2-dimensional area of a profile outlined by an inner surface of the tapered section at a point along the tapered section. Wherein, the plane that the 2-dimensional profile is in is normal (perpendicular) to a longitudinal axis of the tapered section.

Preferably, the tapered section includes supports attached to an outer surface of the truncated cone walls. Most preferably, the supports are in the form of rings.

Inlet and Outlet

The inlet may be positioned at the smaller end of the pipe and the outlet positioned at the larger end of the pipe. Preferably, the inlet is positioned at the larger end of the pipe and the outlet is positioned at the smaller end of the pipe. The inlet and outlet may include a hole on the side of the pipe attachable to other pipes. The inlet and outlet may include other pipes protruding from the surface of the pipe. Preferably, the inlet and outlet include flanges for connection to other pipes.

The inlet and outlet may include curved inner surfaces. The inlet and/or outlet may be orientated at an angle to the pipe. For example, the longitudinal axis of an inlet and/or outlet pipe may be orientated at anywhere from 0 to 90 degrees to the longitudinal axis of the pipe. The pipe may have an inner surface, hereafter nominated "the pipe's inner surface". The inlet pipe may have an inner surface, hereafter nominated "the inlet pipe's inner surface". The inlet pipe may include a longitudinal axis, hereafter nominated "the inlet pipe longitudinal axis".

The inlet pipe may feed the fluid into the pipe at an angle. The inlet pipe may feed the fluid into the pipe at an angle that is transverse (i.e. between 1-89 degrees relative) to the longitudinal axis of the tapered section. The direction of flow of the fluid from the inlet pipe may enter the pipe tangentially, such that the fluid substantially follows the contour of the pipe's inner surface. The inlet pipe longitudinal axis may be offset relative to the longitudinal axis of the tapered section, such that the respective longitudinal axes do not intersect.

The inlet pipe's inner surface may extend along a longitudinal line parallel to the inlet pipe's longitudinal axis. The inlet may be attached to the pipe at an angle such that the longitudinal line is within 15 degrees of tangent to the pipe's inner surface at a junction between the inlet pipe and the pipe. Preferably, the inlet pipe is attached to the pipe such that the inlet pipe longitudinal axis is within 15 degrees of normal relative to the pipe's inner surface, (normal being a line intersecting a surface at right angles to the surface). Preferably, the inlet pipe longitudinal axis is aligned perpendicular to the longitudinal axis of the tapered section. Preferably, the inlet pipe longitudinal axis intersects the longitudinal axis of the tapered section.

The inlet and/or outlet may include multiple inlets or outlets to the pipe. Preferably, there is one inlet and one outlet.

The inlet and/or outlet may include a filter or a mesh. The inlet and/or outlet may include a valve.

A section of pipe the inlet or outlet are attached to may be in the shape of a truncated cone. Preferably, the section of pipe the inlet and outlet are attached to takes the form of a cylinder.

BRIEF DESCRIPTION OF THE DRAWINGS

The invention may be better understood from the following non-limiting description of preferred embodiments, in which:

FIG. 9 is a view of the profiles of a laser beam at angles inside an inner profile of a point along a tapered section of the disinfection device.
FIG. 10 is the close up (view A) of FIG. 9.

DETAILED DESCRIPTION OF THE DRAWINGS

Figure 1:
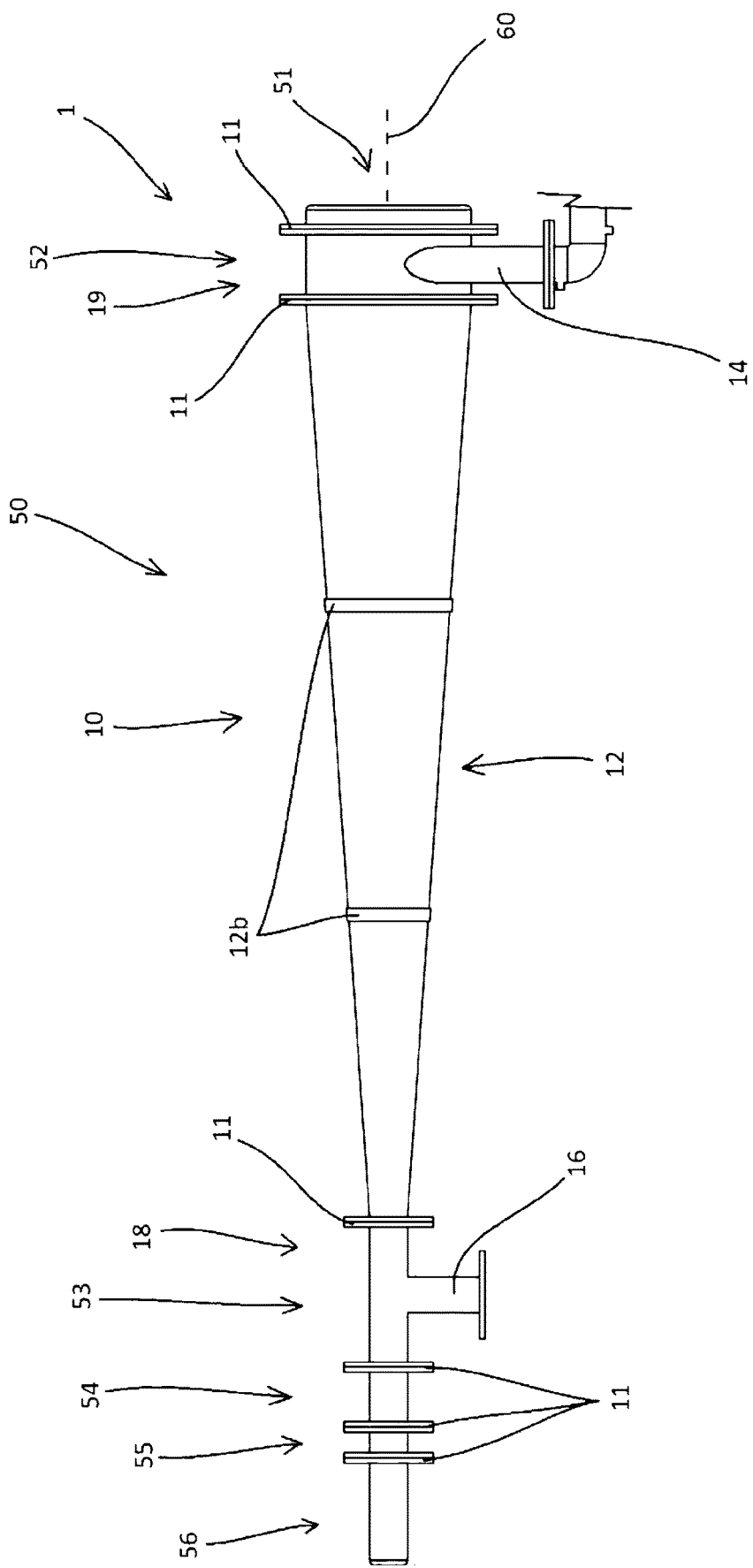
FIG. 1 is a top view of the disinfection device.
Figure 2:
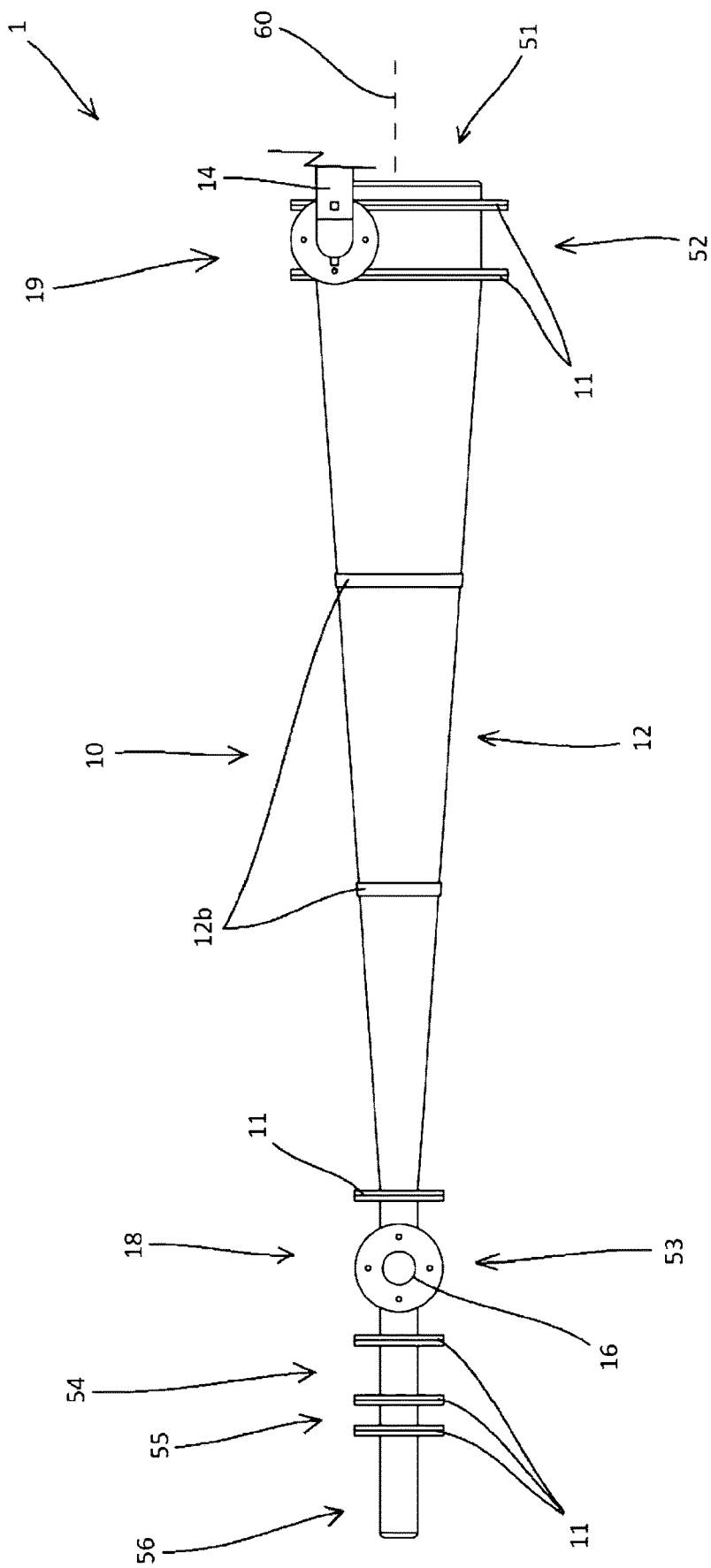
FIG. 2 is a front view of the disinfection device.
Figure 3:
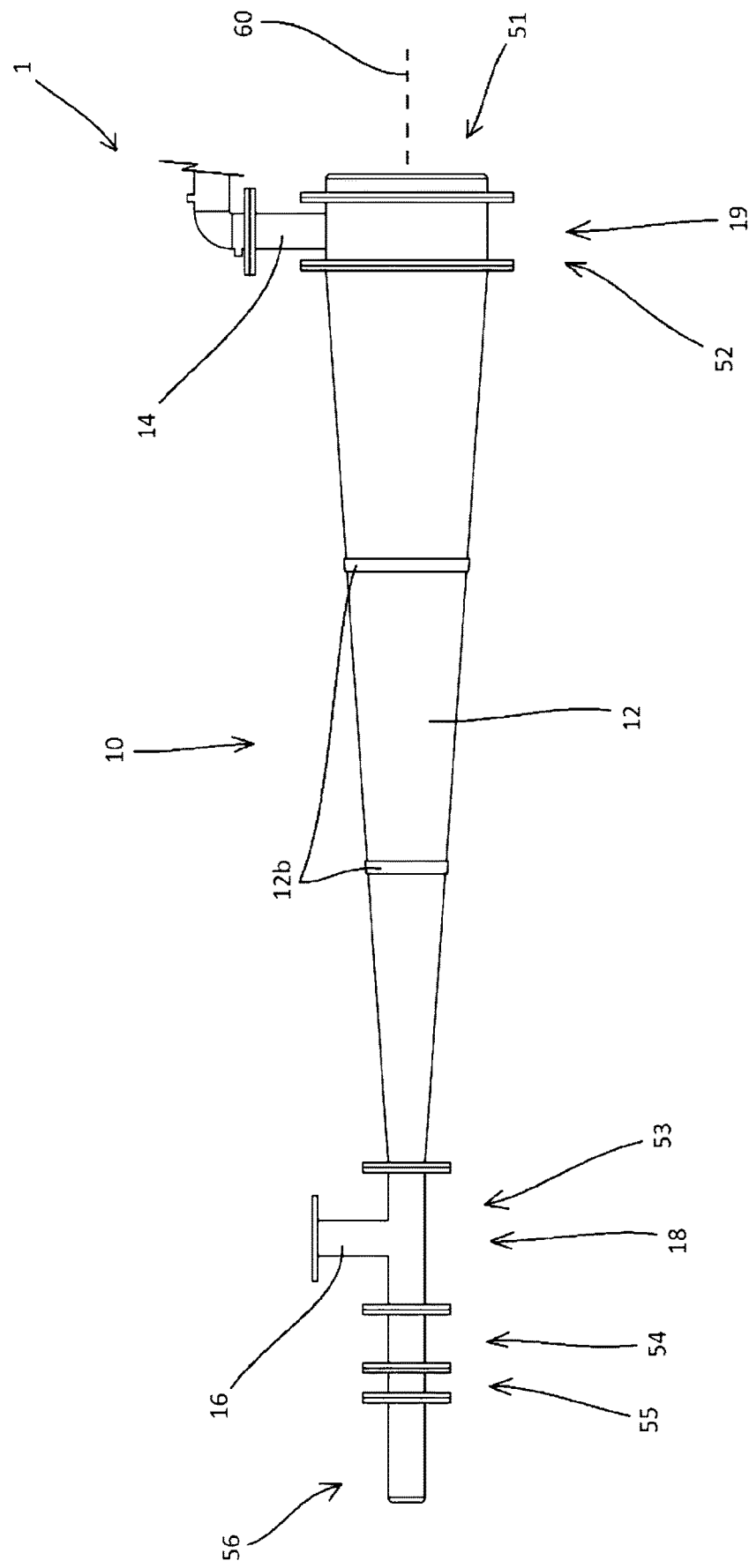
FIG. 3 is a bottom view of the disinfection device.
Figure 4:
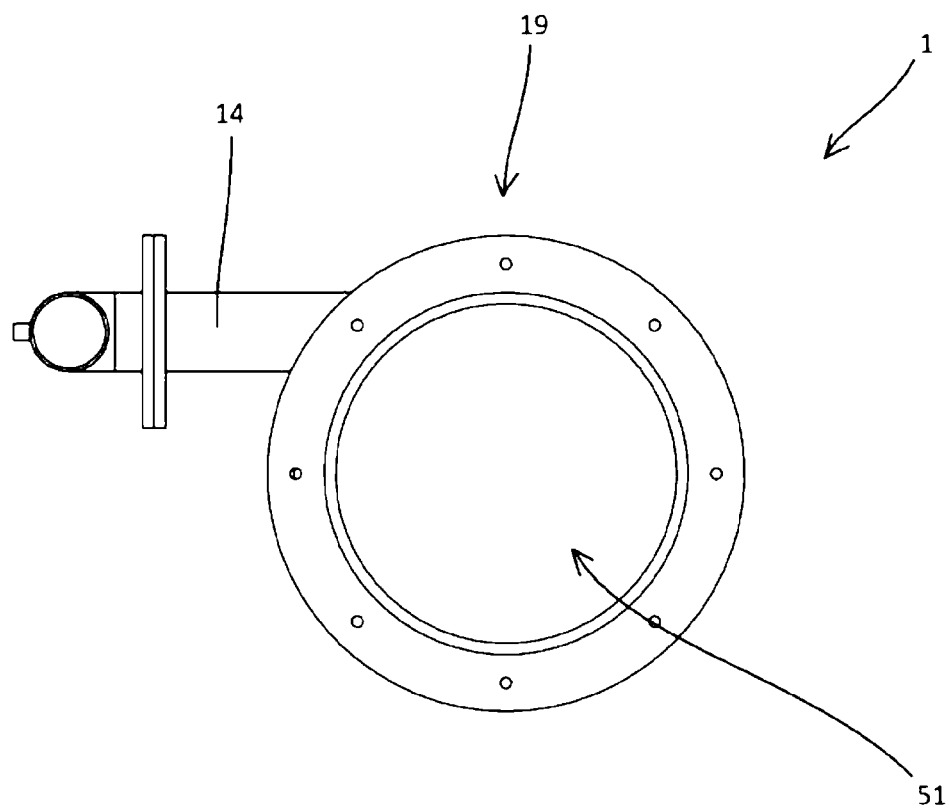
FIG. 4 is a right view of the disinfection device.
Figure 5:
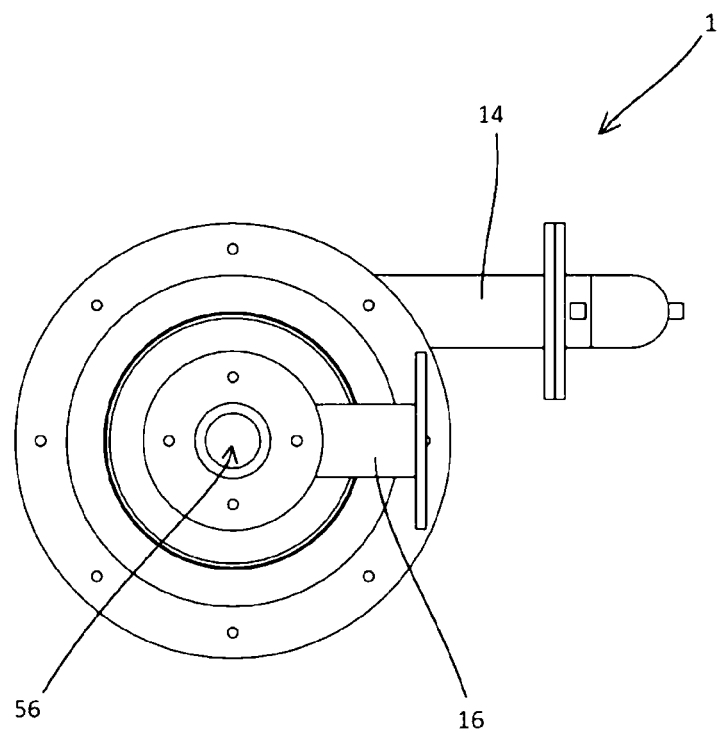
FIG. 5 is a left view of the disinfection device.
Figure 6:
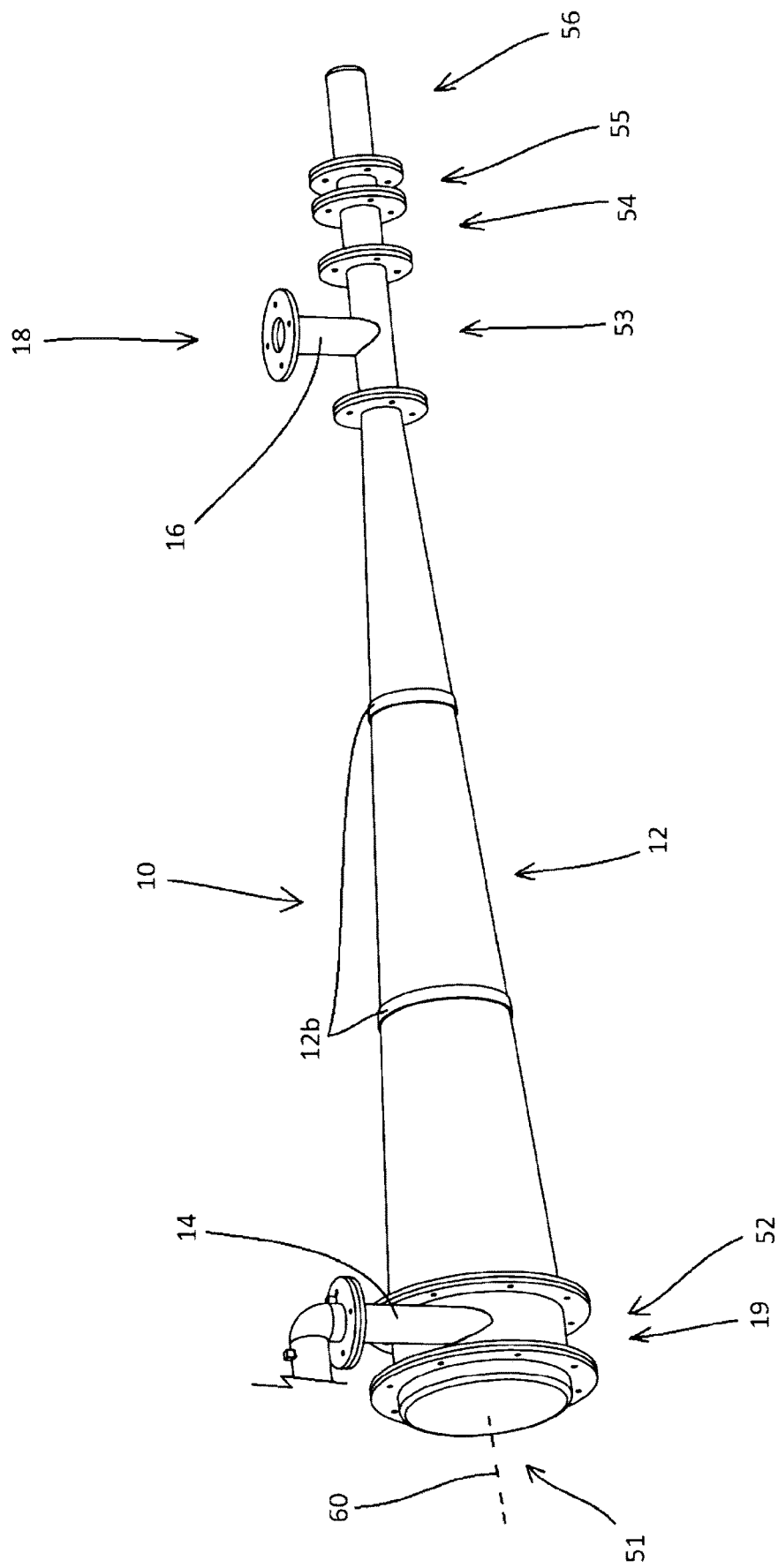
FIG. 6 is a perspective view of the disinfection device.

In describing the various embodiments of the invention, like features will be referred to using like references, with references for features of each embodiment generally preceded by 1, 2, 3, or followed by a Roman numeric sequence, such as i, ii, iii, etc. or an alphabetical sequence such as a, b, c, relative to the corresponding feature of the first embodiment. For example, a feature 10 of the first embodiment may represented as 110, 210, 310, or 10*a*, 10*b*, 10*c*, or 10*i*, 10*ii*, 10*iii*, etc. in second, third and fourth embodiments, respectively.

Preferred features of the present invention will now be described with particular reference to the accompanying drawings. However, it is to be understood that the features illustrated in and described with reference to the drawings are not to be construed as limiting on the scope of the invention.

A disinfection device 1 including a pipe 10, an ultraviolet (UV) laser 20, a beam steering device 22 and a transparent layer 24. The pipe 10 including a tapered section 12, an inlet 14 and an outlet 16. Wherein, the UV laser 20 is located at a smaller diameter end 18 of the pipe 10 and is adapted to project a laser beam towards a larger diameter end 19 of the pipe 10. The laser beam is adapted to project through the beam steering device 22 and the transparent layer 24 at a plurality of angles in a cycle. The beam steering device 22 is adapted to reflect, refract or deflect the laser beam at the angles such that a profile 30 of the laser beam projects through part or all of an inner profile 32 of a point along the tapered section 12 in the cycle. The pipe 10 is adapted to receive a fluid that enters the inlet 14, passes through the pipe 10 and exits through the outlet 16. One of the inlet 14 or outlet 16 is located at the smaller diameter end 18 of the pipe 10 and the other of the inlet 14 or the outlet 16 is located at the larger diameter end 19 of the pipe 10.

The pipe 10 main be nominated a main pipe 10. The pipe 10 includes sections 50 attached together with flanges 11 and bolts (bolts not shown in figures). The bolts are inserted through the holes in the flanges 11. The flanges also include flange seals. The flange seals are flat gasket seals which are positioned between each flange 11.

In a preferred form, the tapered section 12 is a cone shaped section 12.

The sections 50 include a mirror section 51. The mirror section 51 includes a concave mirror 42 and a UV sensor 44. The concave mirror 42 is only slightly concave such that the laser beams reflect at the same angle they hit the concave mirror 42 relative to a longitudinal axis 60 of the cone shaped section 12. The UV sensor 44 is located on the concave mirror 42 on a longitudinal axis 60 of the cone shaped section 12 inside the pipe 10. The UV sensor 44 is connected to a computer. The UV sensor 44 detects UV light from the laser beam when the laser beam shines on the UV sensor 44. The data of whether the laser beam is shining on the UV sensor 44 or not is sent to the computer. Furthermore, data about the intensity of light shining on the UV sensor 44 is sent to the computer.

The sections 50 include an inlet section 52. Both the inlet section 52 and the mirror section 51 include flanges 11. The inlet section 52 is attached to the mirror section 51 through the flanges 11. The inlet section 52 includes the inlet 14.

The sections 50 further include the cone shaped section 12. The cone shaped section 12 includes truncated cone walls 12b. The cone shaped section 12 also includes truncated cone baffles 13a which are arranged concentrically resulting in concentric channels 13b. Each truncated cone baffle 13a has different diameters to form the concentric channels 13b. The truncated cone baffles 13a are held in place with vertical baffles 15a and horizontal baffles 15b. The truncated cone baffles 13a are located in the cone shaped section 12, near the larger diameter end 19 of the pipe.

Figure 7:
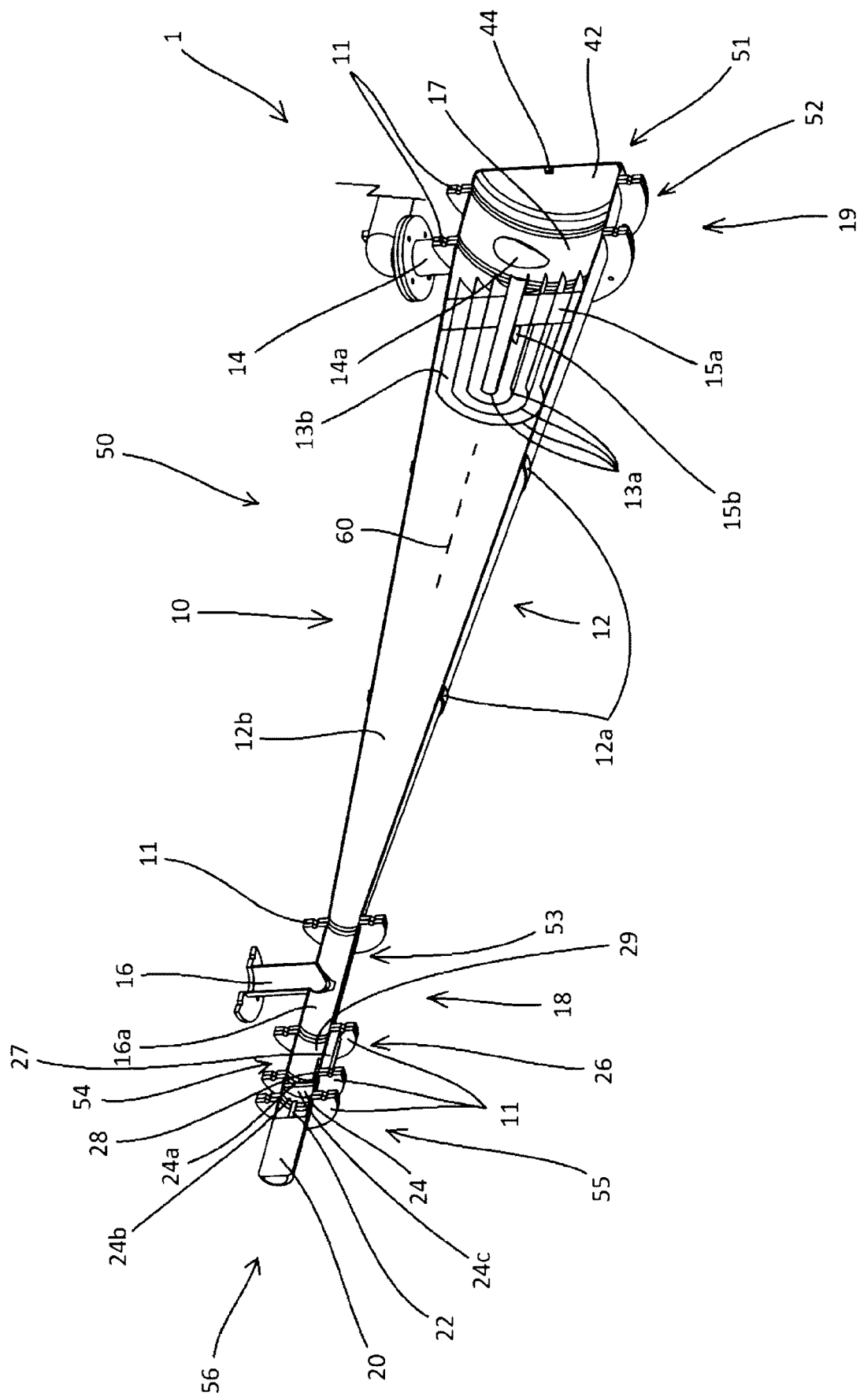
FIG. 7 is a perspective cross sectional view of the disinfection device.
Figure 8:
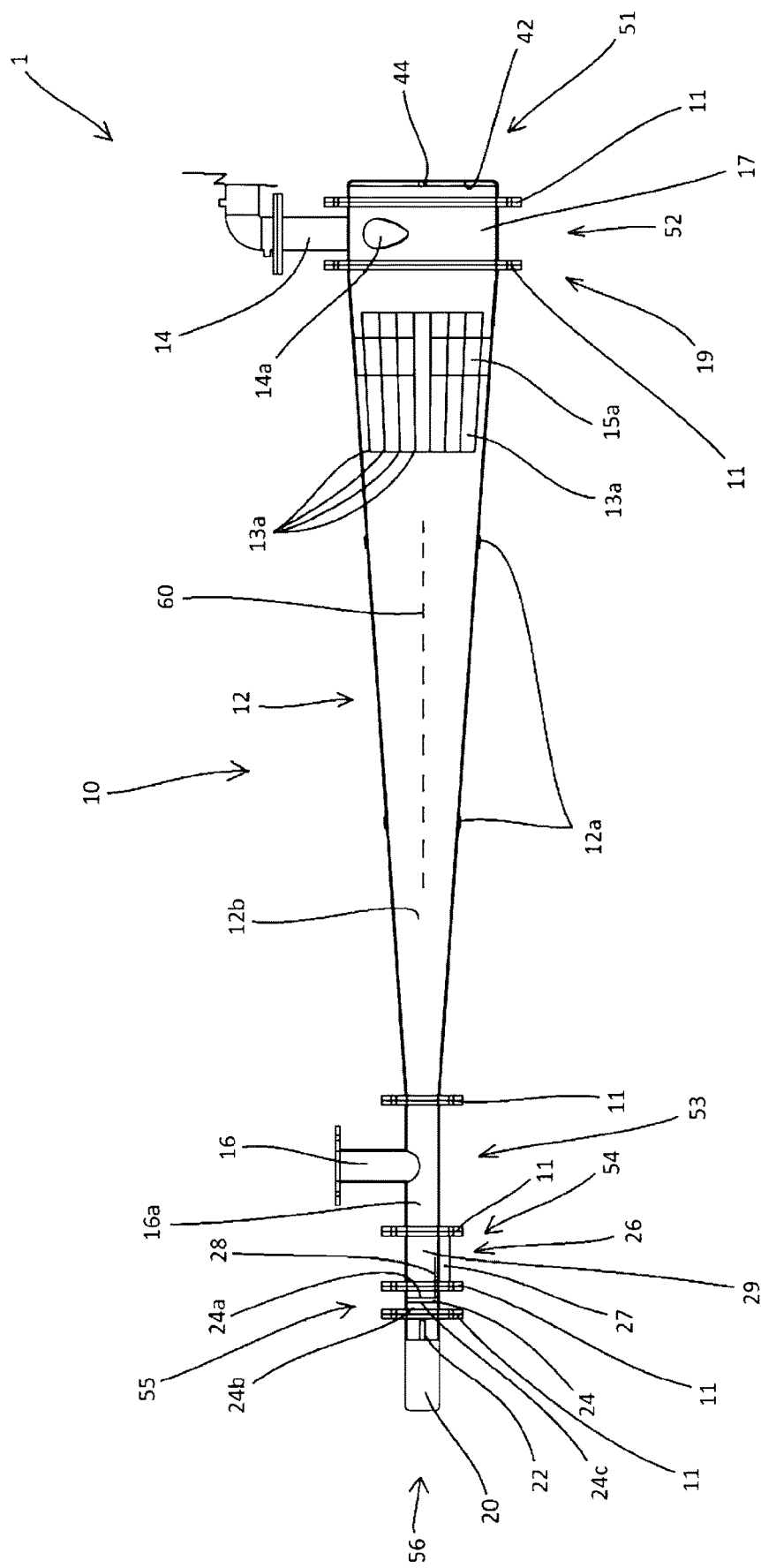
FIG. 8 is a bottom cross sectional view of the disinfection device.

As seen in FIG. 7, the inlet 14 is attached to the pipe 10 at an angle such that the fluid enters the pipe 10 from the inlet 14 at an angle tangent to the pipes inner surface 17. Advantageously, the inlet 14 may be attached to the pipe 10 at an angle such that the fluid enters the pipe 10 from the inlet 14 at an angle substantially normal to the pipe's inner surface 17 and/or the longitudinal axis 60. The inlet 14 is located on the larger diameter end 19 of the pipe 10. The inlet is attached to the pipe 10 at an angle such that a longitudinal line along the internal surface 14a of an inlet pipe 14 is tangent to the pipes inner surface 17. Furthermore, a longitudinal axis of the inlet pipe 14a is aligned perpendicular to the longitudinal axis 60 of the cone shaped section 12. The fluid may be water or air. As fluid enters the pipe 10 from the inlet 14, it rotates about the longitudinal axis 60 of the cone shaped section as it moves from the larger diameter end 19 to the smaller diameter end 18. As the fluid passes through the concentric channels 13b it is kept laminar inside the concentric channels 13b. Keeping the flow of fluid through the pipe laminar keeps the fluid at a similar radial position as it travels through the pipe. This results in a more consistent disinfection of the fluid as the laser beam is more likely to shine through every fluid particle without the fluid particles moving radially during the cycle. Furthermore, the vertical baffles 15a reduce the rotational movement of fluid particles passing through the pipe which also results in a more consistent disinfection of the fluid as the laser beam in more likely to shine through every fluid particle without the fluid particles moving rotationally (about the longitudinal axis 60 of the cone shaped section 12) during the cycle.

The cone shaped section 12 further includes 2 supports 12a. The supports 12a are rings welded to an exterior surface of the cone shaped section 12. The supports 12a provide structural support to truncated cone walls 12b of the cone shaped section 12. By increasing the thickness of the truncated cone walls 12b at certain points along the length of the truncated cone walls 12b (through use of the supports 12a), the truncated cone walls 12b have a higher resistance to radial deformation. There are 2 rings included in the supports 12a and they are located at one third the length of the truncated cone walls 12b and two thirds the length of the truncated cone walls 12b. The cone shaped section 12 is attached to the inlet section 52 with bolts through flanges 11.

The sections 50 also include an outlet section 53. The outlet section 53 includes the outlet 16 and is attached to the cone shaped section 12 with bolts through flanges 11. The outlet 16 is a pipe welded to an outlet section pipe 16a. The outlet 16 is orientated perpendicular to a longitudinal axis of the outlet section pipe 16a.

The sections 50 also include a transparent layer cleaner section 54. The transparent layer cleaner section 54 is attached to the outlet section 53 with bolts through flanges 11. The transparent layer cleaner section 54 includes a transparent layer cleaner 26. The transparent layer cleaner 26 includes an external cleaner device 27 and an internal wiper 28. The external cleaner device 27 is located on an outer surface of a transparent layer cleaner pipe 29. The internal wiper 28 is located on an internal surface of the transparent layer cleaner pipe 29. The external cleaner device 27 uses a magnetic field to actuate the internal wiper 28. The internal wiper 28 doesn't obstruct the path of the laser beams when it is not actuated. When the internal wiper 28 is actuated it slides over (or wipes) the internal side 24a of the transparent layer 24 cleaning any build up of material on the internal side 24a of the transparent layer 24. The transparent layer cleaner 26 is connected to the computer. The computer controls when the transparent layer cleaner 26 is actuated.

The sections 50 further include a transparent layer section 55. The transparent layer section 55 is attached to the transparent layer cleaner section 54 through bolts through flanges 11. The transparent layer section 55 includes the transparent layer 24. The transparent layer 24 is a circular piece of quartzite glass. The transparent layer 24 may be held in place inside a transparent layer pipe 24b and seals the internal side 24a from an external side 24c of the transparent layer with a clamp, glue, fixed by screws or bolts or similar attachment means.

The sections 50 further include a laser section 56. The laser section 56 is attached to the transparent layer section 55 with bolts through flanges 11. The laser section 56 includes the UV laser 20 and the beam steering device 22. The UV laser 20 emits a beam of ultraviolet light with a wavelength of between 100 nm and 300 nm. For example, the UV laser 20 may only emit UV light with a wavelength of 200 nm. The UV laser's beam may have a laser beam profile with a diameter of above 1 mm. For example, the UV laser may have a laser beam profile 30 with a diameter of 3 mm. The beam steering device 22 includes 2 mirrors which are moveable with electric motors. The 2 mirrors reflect the laser beam at any of a continuous set of rotational angles (rotating about the longitudinal axis 60 of the cone shaped section 12) and any of a continuous set of radial angles (extending radially outwards from the longitudinal axis 60 of the cone shaped section 12) up to the radial angle of the truncated cone walls 12b from the longitudinal axis 60 of the cone shaped section 12. The largest radial angle the laser beam is reflected at is the same as the angle of the truncated cone walls 12b from the longitudinal axis 60 of the cone shaped section 12. The 2 mirrors reflect the laser beam at an angle such that the laser beam profile 30 (profile of the laser beam) can shine on at least 99% of a surface of the concave mirror 42 in the cycle. The UV laser 20 and the beam steering device 22 are both powered by electricity and are connected to the computer. The computer controls when the UV laser 20 is turned on or off and at what rotational angle and radial angle the beam steering device 22 projects the laser beam at.

Figure 11:
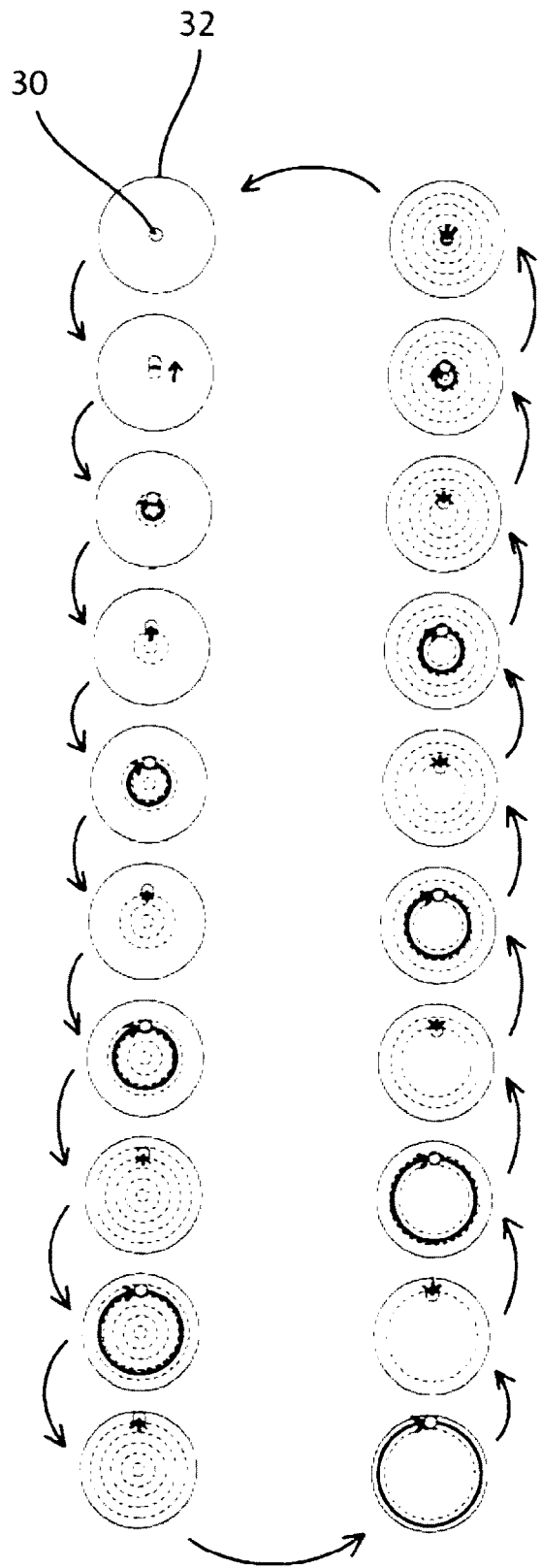
FIG. 11 is an example of the direction the profiles of the laser beam take over time inside the inner profile of a point along the tapered section during a cycle of the disinfection device.

The UV laser 20 is used to treat the fluid in the cone shaped section 12 by moving its angular offset from the longitudinal axis 60 of the cone shaped section 12 and rotating about the longitudinal axis 60 of the cone shaped section 12. FIG. 11 shows an example of how the laser beam profile 30 moves to entirely treat the fluid in the cone shaped section. Initially the UV laser is emitting parallel to the longitudinal axis 60 of the cone shaped section 12. Then the laser beam radial angle is increased and rotated around the longitudinal axis 60 of the cone shaped section 12. This process is repeated until an inner profile of the large diameter end 19 of the cone shaped section 12 has been completely (above 99% of the area of a profile 32 of a point along the cone shaped section 12) exposed to UV light. This completes a cycle. The UV laser 20 then returns to the initial angle (emitting parallel to the longitudinal axis 60 of the cone shaped section 12) and the cycle repeats. The UV laser 20 may rotate clockwise, anticlockwise or may move in any pattern that achieves statistically full coverage or full exposure of the fluid flowing through the cone shaped section 12.

The retention time (time taken for the fluid to pass through the pipe 10) of the pipe 10 is dependent on the flow rate of fluid through the pipe 10 and the size of the pipe 10. Equation 1 calculates the retention time for the reactor.

$$RT = \frac{V}{Q} \quad \text{Equation 1}$$

Where:
RT is the retention time of the pipe 10 in seconds.
V is the volume of the pipe 10 in m³.
Q is the flow rate through the pipe 10 in m³/s.

The retention time of fluid through the concentric channels 13b is dependent on the flow rate of fluid through the concentric channels 13b and the size of the concentric channels 13b. Equation 2 calculates the retention time for fluid through the concentric channels 13b.

$$RT_L = \frac{V_L}{Q_L} \quad \text{Equation 2}$$

Where:
$RT_L$, is the retention time through the concentric channels 13b in seconds.
$V_L$ is the volume of the concentric channels 13b in m³.
$Q_L$, is the flow rate through the concentric channels 13b in m³/s.

To treat the fluid to a satisfactory standard it is preferred, but not entirely necessary, to ensure the time it takes to complete the cycle is less than or equal to the retention time of fluid through the concentric channels 13b.

The disinfection capability of the system can be estimated using the following Equations 3 to 5.

The intensity of the laser beam can be calculated from the power output and area of the beam using Equation 3.

$$I = \frac{P}{A} \quad \text{Equation 3}$$

Where:
I is the intensity of the UV laser 20 in mW/cm².
P is the power of the laser beam in milliwatts.
A is the cross-sectional area of the beam in cm².

Because the UV laser 20 treats a radiated zone of fluid within the cone shaped section 12 at a given time, using the retention time of the cone shaped section 12 is not appropriate when calculating dosage rates. A new term presented for this invention is the Dwell Time (Equation 4). The Dwell Time represents the period of time a laser beam takes to move a distance equivalent to its effective diameter (or diameter of the laser beam). It is dependent on the diameter of the laser beam, or lateral dimensions of the laser beam and the velocity the beam is moved, laterally (with respect to the longitudinal axis 60 of the cone shaped section 12), through the fluid by the beam steering device 22. For a conservative calculation of the Dwell Time, the velocity of beam motion rotating about the longitudinal axis 60 of the cone shaped section 12, at the farthest point from the longitudinal axis 60 of the cone shaped section 12 can be used. For a less conservative calculation, a radial location closer to the longitudinal axis 60 of the cone shaped section 12 may be used.

$$DT = \frac{\o}{V} \quad \text{Equation 4}$$

Where:
DT is the Dwell Time in seconds.
ø is the average radial diameter of the UV laser beam about the longitudinal axis 60 of the cone shaped section 12 in metres in the cycle.
V is the planar velocity the UV laser beam is travelling across the inner profile of the cone shaped section 12 in m/s.

The dose of UV radiation the water is treated with, is calculated with Equation 5 as outlined in Metcalf & Eddy (2003).

$$D = I \times t \quad \text{Equation 5}$$

Where:
D is the UV laser beam dose in mJ/cm².
I is the UV laser beam intensity in mW/cm².
t is the exposure time in seconds For the presented invention, the exposure time (t) is replaced with the Dwell Time (DT) when calculating the UV dosage provided by the UV laser 20.

Calculated dosage may be compared to literature, such as USEPA (2006), Table 1.4, to determine the log inactivation capability of the system for target pathogens.

Calculated dosage rate may also be determined by reference to laboratory based testing of the invention.

The diameter of the UV laser beam and its intensity can be selected depending on the application or size of the treatment device and desired UV light dosage rate.

FIGS. 9-10 show the profiles 30 of the laser beam at the angles inside an inner profile 32 of a point along the cone shaped section 12. It should be noted that the profiles 30 of the laser beam shown in FIGS. 9-10 are the profiles 30 at instants in time in the cycle as the laser beam moves continuously and the angles are a continuous range of angles not a discrete set of angles. The profiles 30 of the laser beam shine through over 99% of the area of a profile 32 of a point along the cone shaped section 12.

FIG. 11 is an example of the direction the profiles 30 of the laser beam move in over time inside the inner profile 32 of a point along the cone shaped section 12 during the cycle. As for FIGS. 9-10, FIG. 11 shows the profiles 30 at instants in time in the cycle as the laser beam moves continuously and the angles are a continuous range of angles not a discrete set of angles. FIG. 11 only demonstrates an example of the order the profiles 30 may take in the cycle. The order the profiles 30 of the laser beam take in a cycle is first project parallel with the longitudinal axis 60 of the cone shaped section 12. Then move to project at a radial position slightly further radially outwards from the first position. Then move to project 360 degrees around the longitudinal axis 60 of the cone shaped section 12 at the same radial position. Then this pattern is repeated, continuing out radially until the profile 30 is at an internal surface of the truncated cone walls 12b. Then the laser beam moves slightly radially inward. Then moves to project 360 degrees around the longitudinal axis 60 of the cone shaped section 12 at the same radial position. Then this pattern is again repeated, continuing radially inward until the laser beam is again parallel with the longitudinal axis 60 of the cone shaped section 12. That is the end of the cycle. The cycle is then repeated.

Figure 12:
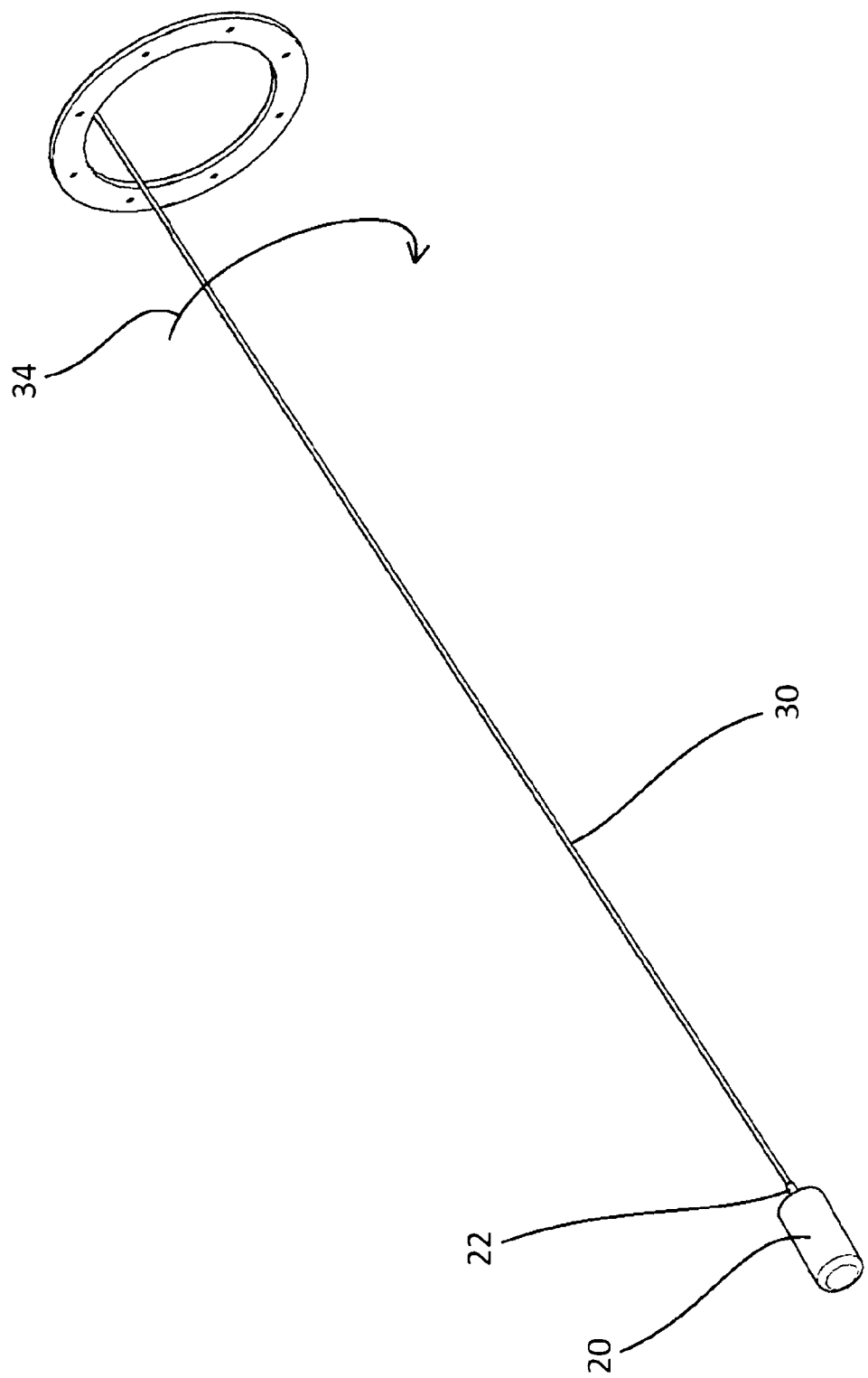
FIG. 12 is a view of the UV laser, beam steering device and a flange of the tapered section with a single laser beam at an instant in time of the cycle.
Figure 13:
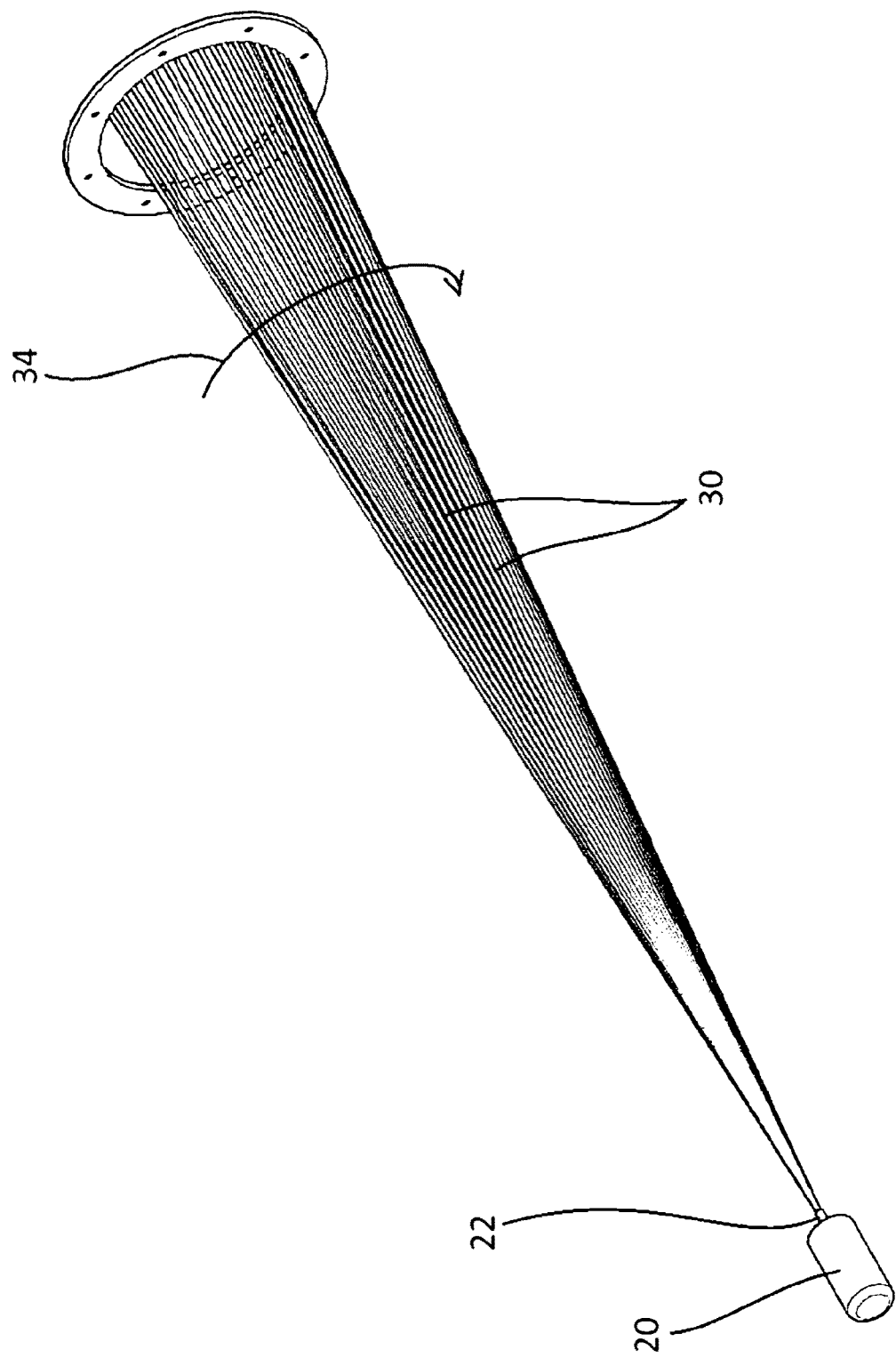
FIG. 13 is a view of the UV laser, beam steering device and the flange of the tapered section with the laser beams at multiple instants in time during the cycle.

FIGS. 12 and 13 show the laser beam at instants in time in the cycle. The arrows 34 show an example of a direction the laser beam may move during the cycle. That direction is rotating about the longitudinal axis 60 of the cone shaped section 12.

The following are references referred to in the detailed description:

Metcalf & Eddy 2003, *Wastewater Engineering: Treatment and Reuse*, 4$^{th}$ edition, McGraw-Hill, New York, N.Y.

US EPA 2006, *Ultraviolet Disinfection Guidance Manual for the Final Long Term 2 Enhanced Surface Water Treatment Rule*, U.S. Environmental Protection Agency Office of Water.

Throughout the specification and claims the word "comprise" and its derivatives are intended to have an inclusive rather than exclusive meaning unless the contrary is expressly stated or the context requires otherwise. That is, the word "comprise" and its derivatives will be taken to indicate the inclusion of not only the listed components, steps or features that it directly references, but also other components, steps or features not specifically listed, unless the contrary is expressly stated or the context requires otherwise.

In the present specification, terms such as "apparatus", "means", "device" and "member" may refer to singular or plural items and are terms intended to refer to a set of properties, functions or characteristics performed by one or more items or components having one or more parts. It is envisaged that where an "apparatus", "means", "device" or "member" or similar term is described as being a unitary object, then a functionally equivalent object having multiple components is considered to fall within the scope of the term, and similarly, where an "apparatus", "assembly", "means", "device" or "member" is described as having multiple components, a functionally equivalent but unitary object is also considered to fall within the scope of the term, unless the contrary is expressly stated or the context requires otherwise.

In the present specification, the phrase "and/or" refers to severally or any combination of the features. For example, the phrase "feature 1, feature 2 and/or feature 3" includes within its scope any one of the following combinations: Feature 1 or feature 2 or feature 3; feature 1 and feature 2 or feature 3; feature 1 or feature 2 and feature 3; feature 1 and feature 3 or feature 2; feature 1 and feature 2 and feature 3.

Orientational terms used in the specification and claims such as vertical, horizontal, top, bottom, upper and lower are to be interpreted as relational and are based on the premise that the component, item, article, apparatus, device or instrument will usually be considered in a particular orientation, typically with the inlet 14 uppermost.

The meaning of descriptive, precise or absolute terms such as "flexed", "normal", "parallel", "horizontal", "vertical" or "fully" includes the preceding qualifier "substantially or almost", unless the context or contrary is expressly indicated.

Qualifying relative terms, such as "relatively", "sufficiently", "near", "almost" or "substantially", may be taken to indicate a variation in an absolute value of between 0° and 10° or between 0% and 10%, relative to the absolute value. For example, "near horizontal" may be taken to mean any orientation between 0° and 10° relative to the horizontal.

In the present specification, the term "integral" means formed of one body in a single process. In particular, the term "integrally formed" means formed of the one body without post-forming attachment of separately formed component parts. That is, "integrally formed" and the similar term "unitarily formed" mean formed in a single forming process and do not include post-forming attachment of component parts by means of fastener or other component fixing substances or methods.

It will be appreciated by those skilled in the art that many modifications and variations may be made to the methods of the invention described herein without departing from the spirit and scope of the invention.

It will be appreciated by those skilled in the art that many modifications and variations may be made to the methods of the invention described herein without departing from the spirit and scope of the invention. The features and components of each of the embodiments of the invention described in the detailed description and/or depicted in the accompanying drawings may be interchangeable as required, with regard to functional equivalency and compatibility. A feature or component described with reference to one but not all embodiments, if functionally and dimensionally compatible as an addition with another embodiment herein described, or substitutable with a corresponding feature or component of that other embodiment in relation to which it has not been expressly described, should be read as a potential addition or substitution to that other embodiment and as being within the scope of the invention. Furthermore, in considering a feature or component that is described in relation a particular embodiment but may be omitted from the embodiment without losing the functionality characterising the invention and without departing from the scope of the invention, unless the context and expressions used in describing the embodiment imputes that the feature or component is essential to the invention as broadly described, the omittable feature or component may be read as not being included in the embodiment.

The claims defining the invention are as follows:

1. A disinfection device including a pipe, an ultraviolet (UV) laser, a beam steering device and a transparent layer, the pipe including,
   an inlet and an outlet, wherein:
   the pipe includes a tapered section adapted to receive a fluid flowable through the pipe;
   the tapered section is adapted to be exposed to a focused laser beam for disinfection of the fluid;

the UV laser is located at a smaller diameter end of the pipe and is adapted to project the focused laser beam towards a larger diameter end of the pipe;

the focused laser beam is adapted to project through and/or off the beam steering device and through the transparent layer at a plurality of angles in a cycle in which the focused UV laser is adapted to move in a pattern that achieves statistically full coverage or full exposure of the fluid that flows through the tapered section;

the beam steering device is adapted to steer the laser beam at the angles such that a profile of the focused laser beam projects through part or all of an inner profile of a point along the tapered section in the cycle, the inner profile of the tapered section being a 2-dimensional profile taken through a cross-section of the pipe;

the pipe is adapted to receive a fluid that enters the inlet, passes through the pipe and exits through the outlet;

one of the inlet or the outlet is located at the smaller diameter end of the pipe and the other of the inlet or the outlet is located at the larger diameter end of the pipe; and wherein, the pipe includes fins or channels in the tapered section, the UV laser projecting the focused UV beam towards the fins or channels in an alignment parallel to the fins or channels and to the flow of fluid through the pipe.

2. The disinfection device as claimed in claim 1, wherein, the channels are made of concentric truncated cones held concentrically with radial panels.

3. The disinfection device as claimed in claim 1, wherein, the tapered section is a truncated cone shaped section.

4. The disinfection device as claimed in claim 1, wherein, the inlet includes an inlet pipe, the inlet pipe is attached to the pipe such that a longitudinal axis of the inlet pipe is within 15 degrees of normal to an inner surface of the pipe where the inlet pipe meets the pipe.

5. The disinfection device as claimed in claim 4, wherein, the inlet pipe is attached to the pipe such that a longitudinal axis of the inlet pipe is normal to an inner surface of the pipe where the inlet pipe meets the pipe.

6. The disinfection device as claimed in claim 1, wherein, the wavelength of light which projects from the UV laser is between 100 nm (nanometers) and 300 nm.

7. The disinfection device as claimed in claim 1, wherein, the beam steering device includes 2 mirrors adapted to reflect the beam at any of a continuous set of rotational angles rotating about a longitudinal axis of the tapered section.

8. The disinfection device as claimed in claim 1, wherein, the disinfection device includes a UV sensor positioned in line with a longitudinal axis of the tapered section to detect when the transparent layer needs cleaning by a transparent layer cleaner.

9. The disinfection device as claimed in claim 1, wherein, the disinfection device includes a concave mirror at the larger diameter end of the pipe.

10. The disinfection device as claimed in claim 3, wherein, the tapered section includes supports in the form of rings attached to an outer surface of the truncated cone shaped section, the rings providing structural support to walls of the truncated cone shaped section, the thickness of the truncated cone walls increased at certain points along the length of the truncated cone walls to provide a higher resistance to radial deformation.

11. The disinfection device as claimed in claim 8, wherein, the disinfection device includes a UV sensor to detect when the transparent layer needs cleaning by a transparent layer cleaner that includes mechanical wipers which contact a surface of the transparent layer in contact with the fluid.

12. The disinfection device as claimed in claim 1, wherein, the length of the pipe is above 500 mm.

13. The disinfection device as claimed in claim 1, wherein, the transparent layer is made of materials including quartzite and a transparent layer cleaner is provided which is adapted to burn and therefore clean debris off the transparent layer and/or a mirror adapted to reflect the beam at any of a continuous set of rotational angles rotating about a longitudinal axis of the tapered section.

14. The disinfection device as claimed in claim 1, wherein, the pipe includes sections attached together with flanges.

15. The disinfection device as claimed in claim 1, wherein, the plurality of angles are any radial angle extending radially outwards from a longitudinal axis of the tapered section up to an angle of a wall of the tapered section.

16. The disinfection device as claimed in claim 1, wherein, the beam steering device is capable of steering or redirecting the laser beam with little or no loss of intensity at a zone of re-direction or reflection.

17. The disinfection device as claimed in claim 1, wherein, the device includes a second laser which is adapted to burn and therefore clean debris off the transparent layer and/or a mirror adapted to reflect the beam at any of a continuous set of rotational angles rotating about a longitudinal axis of the tapered section.

18. The disinfection device as claimed in claim 1, wherein, the pipe includes a laminar device in the form of fins or channels to keep the flow through the pipe laminar.

19. The disinfection device as claimed in claim 18, wherein, the laminar device comprises channels that are made of concentric truncated cones held concentrically with radial panels.

20. The disinfection device as claimed in claim 19, wherein, the laminar device extends part of the length of the tapered section.

21. The disinfection device as claimed in claim 1, wherein, the UV laser and the beam steering device are connected to a computer which controls at what rotational angle and radial angle the beam steering device projects the laser beam.

22. The disinfection device as claimed in claim 1, wherein, the pipe is adapted to keep the flow of fluid through the pipe laminar to limit radial movement of the fluid particles during the cycle.

23. A disinfection device including a pipe, an ultraviolet (UV) laser, a beam steering device and a transparent layer, an inlet and an outlet, wherein:

the pipe includes a tapered section;

the UV laser is located at a smaller diameter end of the tapered section and is adapted to project a narrow focus laser beam toward a larger diameter end of the pipe;

the laser beam is adapted to project through and/or off the beam steering device and through the transparent layer at a plurality of angles in a cycle, maintaining the narrow focus;

the beam steering device is adapted to steer the laser beam at the angles such that a profile of the laser beam projects through part or all of an inner profile of a point along the tapered section in the cycle, the inner profile of the tapered section being a 2-dimensional profile taken through a cross-section of the pipe;

the pipe is adapted to receive water that enters the inlet, passes through the pipe and exits through the outlet, one of the inlet or the outlet being located at the smaller diameter end of the pipe and the other of the inlet or the outlet being located at the larger diameter end of the pipe; and the UV laser is adapted to move in a pattern through the cycle that achieves statistically full coverage or full exposure of the fluid that flows through the tapered section; and wherein, the pipe includes fins or channels in the tapered section, the UV laser projecting the narrow focus UV beam towards the fins or channels in an alignment parallel to the fins or channels and to the flow of fluid through the pipe.

* * * * *